US00PP12441P2

(12) United States Plant Patent

Bak et al.

(10) Patent No.: US PP12,441 P2
(45) Date of Patent: Mar. 5, 2002

(54) GUZMANIA PLANT NAMED 'COPITO'

(75) Inventors: Elly Bak, Rijsenhout; Nicolaas D. M. Steur, Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 09/572,314

(22) Filed: May 18, 2000

(51) Int. Cl.[7] ..... A01H 5/00
(52) U.S. Cl. ..... Plt./371
(58) Field of Search ..... Plt./371

(56) References Cited

U.S. PATENT DOCUMENTS

PP8,996 P * 11/1994 Bak et al. ..... Plt./371
PP11,893 P2 * 5/2001 Bak et al. ..... Plt./371

OTHER PUBLICATIONS

GTITM UPOVROM Citation for 'Copito' as per QZ PBR 000177; Mar. 13, 2000.*
Benzing, David H., "The Biology of the BROMELIADS", Mad River Press, Eureka, CA, pp. 1–287 (1980).
Rauh et al., "Bromelien Tillandsien und andere kulturwurdige Bromelian", Eugen Ulmer, Stuttgart, Germany, pp. 7–68 (1981).
Zimmer et al., "Bromelien Botanik und Anzucht ausgewahlter Arten", Parey, Berlin; Hamburg, Germany, pp. 9–94 (1986).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A Guzmania plant named 'Copito' particularly characterized by its solid growth habit in a funnel-form rosette measuring approximately 20 cm in height above the pot when flowering; numerous, relatively narrow leaves, each approximately 2–2.5 cm in width and 25 cm in length; superior floral bract production; compound inflorescence; and long-lasting habit.

2 Drawing Sheets

BACKGROUND OF THE INVENTION

The present invention comprises a new and distinct cultivar of *Guzmania lingulata minor* plant, hereinafter referred to by the cultivar name 'Copito'. The genus Guzmania is a member of the family Bromeliaceae.

Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Desirably, the plants are shaded from direct sunlight, and during the spring to autumn period, the central vase-like part of the leaf rosette is desirably filled with water.

Guzmania is native to tropical America. Leaves of Guzmania are usually formed as basal rosettes, which are stiff and entire and in several vertical ranks. Guzmania plants have terminal spikes or panicles which are often bracted with petals united in a tube about as long as the calyx. The ovary is superior and the seeds plumrose.

Asexual propagation of Guzmania is frequently done through the use of tissue culture practices. Propagation can also be from offshoots produced by the plant which may then be rooted. The resulting plantlets are detached from the mother plant and may be potted in a suitable growing mixture.

Methods for cultivation and crossing of Guzmania are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

The new cultivar 'Copito' is a product of a planned breeding program and was originated by the inventors, Elly Bak and Nicolaas D. M. Steur, from a cross made during such a program in Assendelft, The Netherlands, in 1994. The male or pollen parent was a proprietary selection of *Guzmania lingulata minor* identified by Code No. 94861137. The female or seed parent was a proprietary selection of *Guzmania lingulata minor* identified by Code No. 94861032. Both parents have a degree of homozygosity such that the progeny of the stated cross were and continue to be uniform.

'Copito' is a steady, small-sized, long-lasting hybrid with a star-shaped, white inflorescence. Asexual reproduction of the new cultivar by tissue culture was performed by the inventor in a controlled environment, and has demonstrated that the combination of characteristics as herein disclosed for the new cultivar are firmly fixed and reproduces true to type through successive generations of asexual reproduction.

BRIEF DESCRIPTION OF THE INVENTION

The following traits have been repeatedly observed and are determined to be basic characteristics of 'Copito' which in combination distinguish this Guzmania as a new and distinct cultivar:

1. steady growth habit in a funnel-form rosette measuring approximately 20 cm in height above the pot when flowering;
2. numerous, relatively narrow leaves, each approximately 2–2.5 cm in width and 25 cm in length;
3. superior primary bract production;
4. compound inflorescence;
5. long-lasting leaves and inflorescence color.

'Copito' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

Of the commercial cultivars known to the present inventor, the most similar in comparison to 'Copito' is the cultivar Guzmania 'Rondo' (unpatented). The most important difference is the color of the inflorescence. The inflorescence of Guzmania 'Copito' is white in color while the inflorescence of Guzmania 'Rondo' is red.

In comparison to 'Copito' which has a plant height of approximately 20 cm, the female parental cultivar is approximately 17 cm in height, and the male parental cultivar is approximately 22 cm in height.

BRIEF DESCRIPTION OF THE DRAWING

The accompanying photographic illustrations show a typical 'Copito' plant following growth under appropriate growing conditions, with colors being as true as possible with illustrations of this type.

Sheet 1 is a side view of the inflorescence and foliage characteristics of 'Copito'.

Sheet 2 is a close-up view of the inflorescence of 'Copito'.

DETAILED BOTANICAL DESCRIPTION

The following observations, measurements and descriptions describe 8 to 10 month old plants after potting grown in The Netherlands under greenhouse conditions which approximate those generally used in commercial practice. In the following description, color references are made to The Royal Horticultural Society (R.H.S.) Colour Chart. The new cultivar flowers approximately 9 weeks after treatment with acetylene.

Classification:
- *Botanical.*—*Guzmania lingulata minor.*
- *Commercial.*—Guzmania cv. 'Copito'.

Plant:
- *Form.*—Funnel-form rosette.
- *Height.*—Approximately 20 cm high, when flowering.
- *Growth habit.*—Stemless.
- *Diameter.*—Approximately 40 cm.
- *Crop time.*—It takes approximately 8 to 10 months from potting, to produce a finished flowering plant.

Foliage:
- *Color.*—Upper surface: RHS 137A. Under surface: RHS 137C.
- *Size of leaf.*—Length: Approximately 25 cm. Width: Approximately 2.0–2.5 cm.
- *Shape of leaf.*—Linear-lanceolate.
- *Surface texture.*—Smooth.
- *Apex.*—Acute.
- *Margin.*—Entire.
- *Orientation.*—Leaf blades arch continuously from the base.
- *Number of leaves.*—Approximately 22.

Bracts:
- *Scape bracts.*—Length: Lowest are approximately 15 cm long. The scape bracts just below the primary bracts are approximately 6 cm long. Width: Approximately 2.0–2.5 cm. General Shape: Ovate-lanceolate. Texture: Smooth. Margin: Entire. Apex: Acute. Color: RHS 137A (Both surfaces). Number: Approximately 10.
- *Primary bracts.*—Length: Lowest are approximately 6 cm long. The bracts progress upwardly, they become shorter, with the top primary bracts approximately 3 cm in length. Width: Approximately 1.5–2.0 cm. General Shape: Ovate-lanceolate. Texture: Smooth. Margin: Entire. Apex: Acute. Color: Upper surface RHS 160D, lower surface RHS 137A. Number: Approximately 15.
- *Top primary bracts.*—Apex: Acute. Color: RHS 160D (Both surfaces).
- *Floral bracts.*—Length: Approximately 3 cm. Color: RHS 160 D (Both surfaces).

Flowers:
- *Borne (stalks).*—Erect.
- *Shape of the Inflorescence:*—*Round spike*
- *Number of inflorescences per plant.*—1.
- *Number of flowers per inflorescence.*—Approximately 30.
- *Size of inflorescence on stalk.*—Approximately 6 cm high and approximately 10 cm in diameter.
- *Individual petals.*—(Mostly disposed within the inflorescence). Length: Approximately 5 cm. Width: Approximately 0.5 cm. Quantity: Approximately 30 flowers depending on the size of the plant. Color: White, RHS 155D (Both surfaces).
- *Time of blooming.*—A fully grown plant can bloom throughout the entire year starting approximately nine (9) weeks after natural induction or through treatment with acetylene.
- *Duration of blooms.*—Each flower blooms one (1) day and the total of blooming time for one plant is approximately five (5) weeks.

Reproductive organs:
- *Ovaries.*—Superior.
- *Stamens.*—Six (6) in number.

Seed characteristics: hybrid, therefore, seeds cannot be used for reproduction.
- *Quantity.*—Approximately 4000 seeds divided over approximately 15 capsules (depending on the size of the plant).
- *Texture.*—Plumrose.
- *Color.*—RHS 165B.
- *Pappus color.*—RHS 165D.
- *Length.*—Approximately 3 mm.
- *Diameter.*—Approximately 0.3 mm.

Disease/pest resistance/susceptibility: No observations made to date.

We claim:

1. A new and distinct cultivar of Guzmania plant named 'Copito' substantially as illustrated and described.

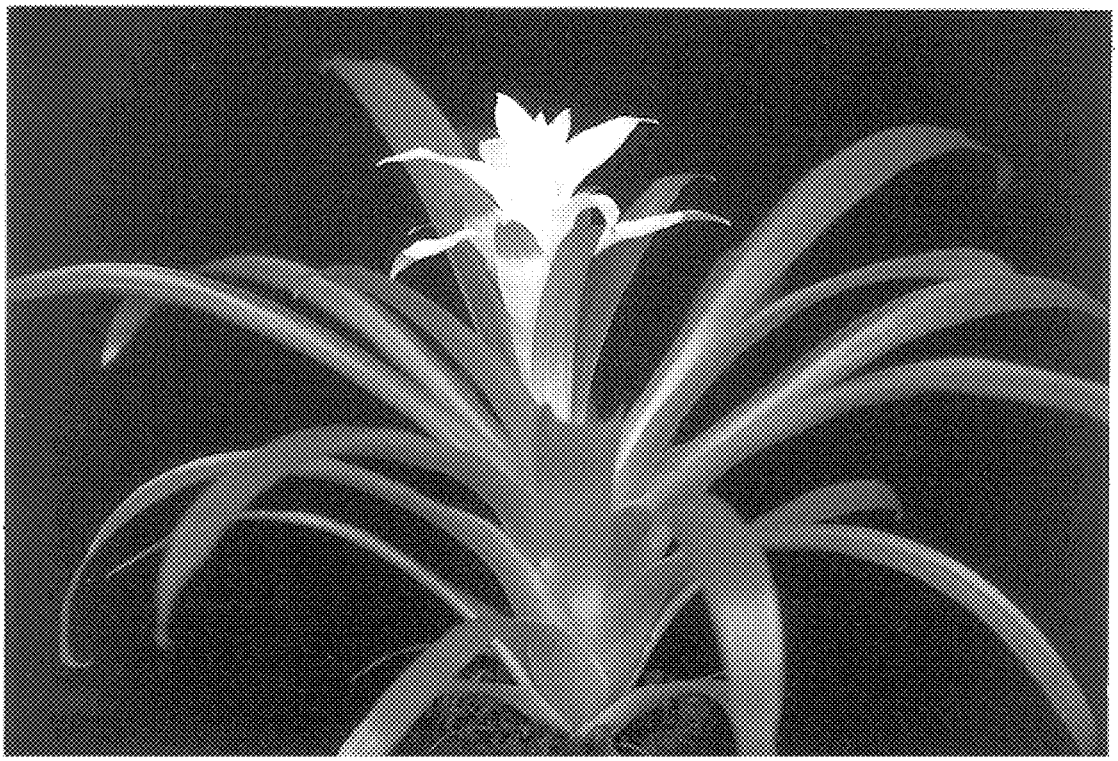

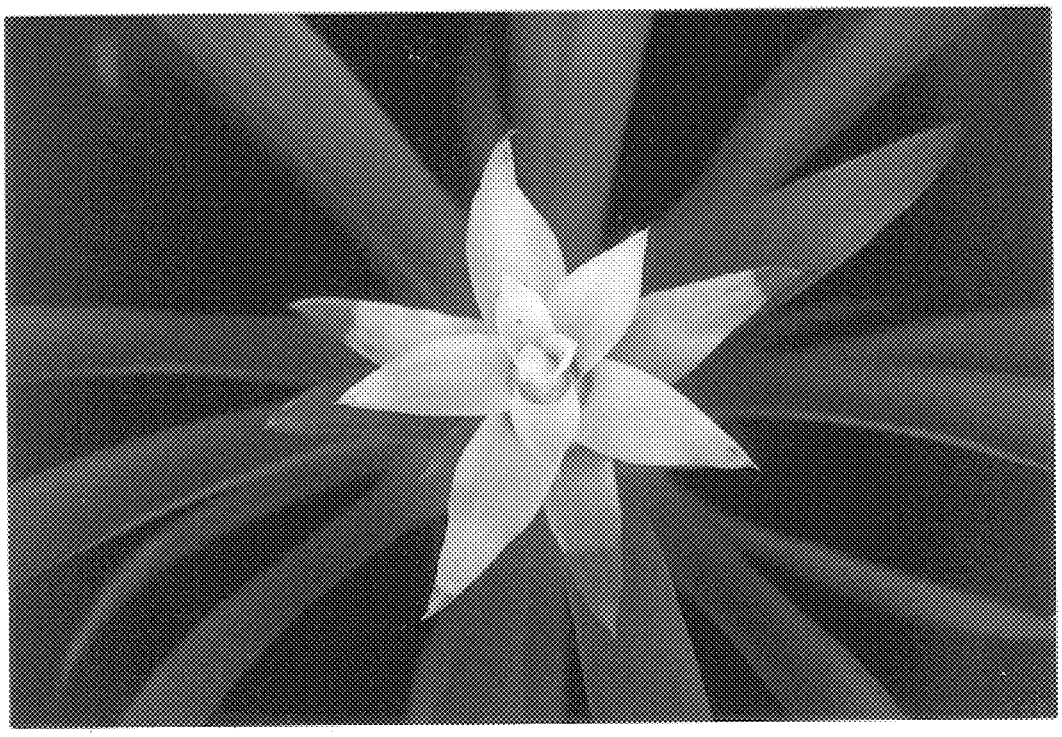

* * * * *